United States Patent [19]
Onotsky

[11] Patent Number: 5,275,284
[45] Date of Patent: Jan. 4, 1994

[54] BANDAGE AND PACKAGING THEREFOR

[76] Inventor: Ken R. Onotsky, P.O. Box 1990, Hwy 576, Timmins, Ontario, Canada, P4N 7X8

[21] Appl. No.: 63,695

[22] Filed: May 20, 1993

[51] Int. Cl.$^5$ ............................................. A61B 17/06
[52] U.S. Cl. ................................... 206/441; 206/469; 383/202; 602/57
[58] Field of Search ............... 206/441, 440, 447, 469; 383/202; 602/42, 57

[56] References Cited

U.S. PATENT DOCUMENTS

| | | |
|---|---|---|
| 2,132,741 | 10/1938 | Kyseth . |
| 2,140,021 | 12/1938 | Mallen . |
| 2,927,689 | 3/1960 | Look, Jr. . |
| 2,973,859 | 3/1961 | Schladermundt et al. ......... 206/441 |
| 3,545,604 | 12/1970 | Gunther, Jr. . |
| 3,730,336 | 5/1973 | Feldman . |
| 3,899,077 | 8/1975 | Spiegelberg ........................ 206/441 |
| 3,900,105 | 8/1975 | Wolfesperger ..................... 206/469 |
| 4,265,234 | 5/1981 | Schaar ............................... 206/441 |
| 4,281,650 | 8/1981 | Spiegelburg ....................... 206/440 |
| 4,739,881 | 4/1988 | Bruso ................................. 383/202 |
| 4,884,563 | 12/1989 | Sessions ............................. 206/441 |

Primary Examiner—David T. Fidei
Attorney, Agent, or Firm—Nixon & Vanderhye

[57] ABSTRACT

A prepackaged adhesive bandage in a protective envelope includes a semi-rigid backing strip adhered to the bandage, and a flexible backing interconnected between the bandage and the envelope seam. The semi-rigid strip is manipulated to penetrate the envelope face, permitting the strip and attached bandage to be withdrawn from the envelope. The retained flexible backing is peeled from the bandage during withdrawal, exposing an adhesive surface for application of the bandage to the skin.

17 Claims, 2 Drawing Sheets

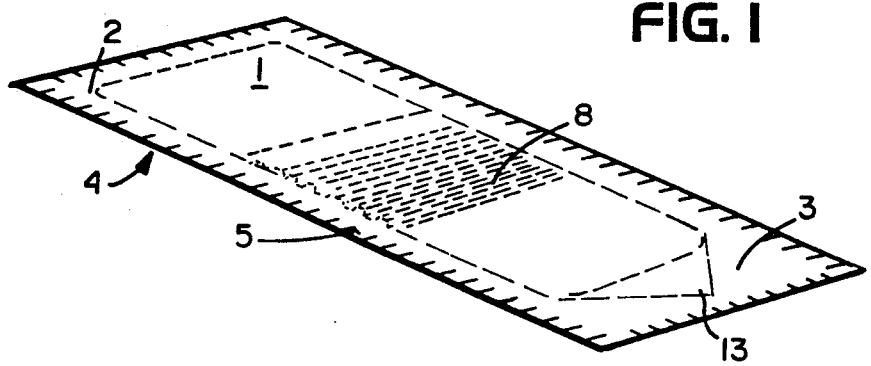
FIG. 1
FIG. 2
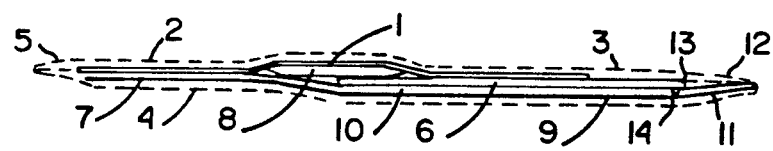
FIG. 2A
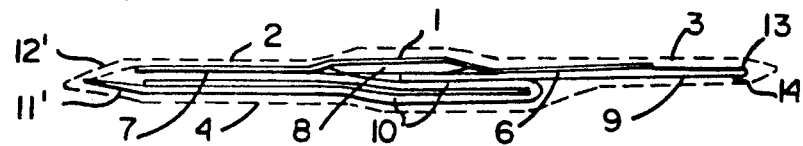
FIG. 3
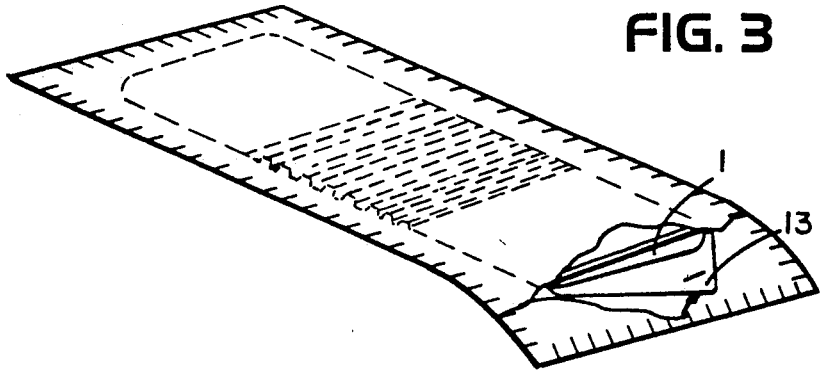
FIG. 4
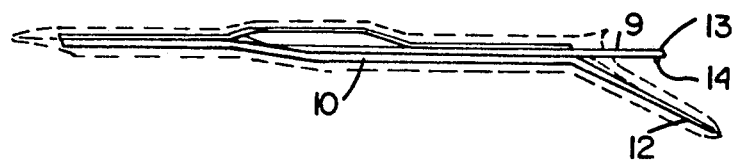

FIG. 5
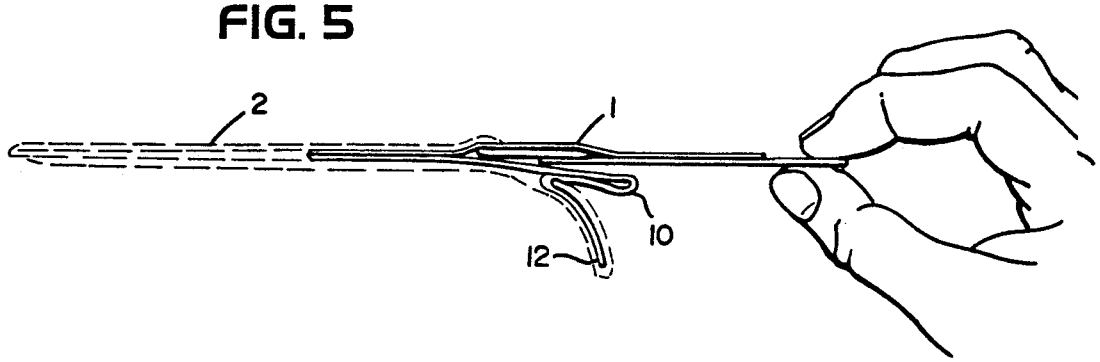
FIG. 6
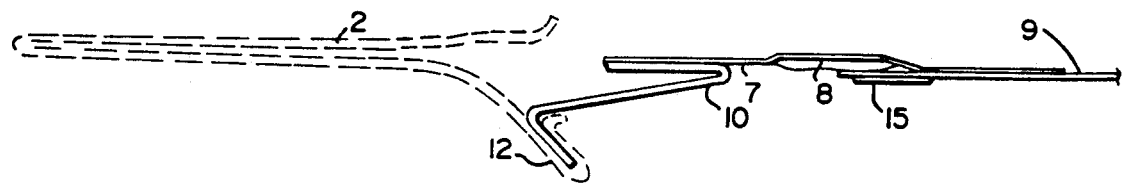
FIG. 7
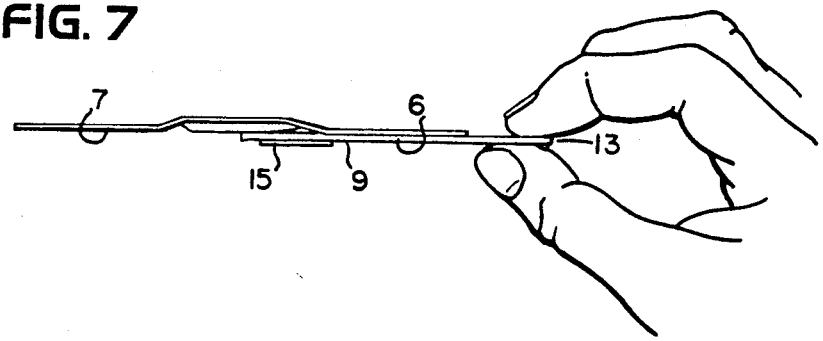
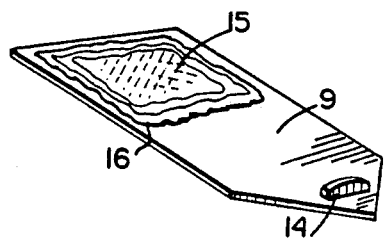
FIG. 8

BANDAGE AND PACKAGING THEREFOR

BACKGROUND OF THE INVENTION

The present invention relates to a prepackaged self adhesive individual bandage and a method of opening such a bandage package. The bandage structure uses a semi-rigid strip within the package envelope to pierce the envelope and to serve as a grip to remove the bandage and to guide the bandage during application. The present invention provides for a device for rapid and convenient dispensing of a conventional type of bandage having a strip of adhesive tape with or without a central gauze pad. The adhesive surface and gauze surface is protected from contamination by removable protective backing strips. The present invention also reduces the quantity of refuse remaining after the application of the bandage.

Typically conventional bandages are individually packaged in sealed envelopes which may be made of paper or plastic film, and may be opened by one of several different methods. In one type of package, the envelope is completely sealed or bonded around the perimeter. Such package is opened by tearing an end or side open to permit removal of the bandage contained inside. In a second type of package the two opposed surfaces of the envelope extend, at one end, beyond the bonded portion, leaving two flaps which may be pulled in opposite directions to split the envelope seal. The flaps may be folded back to facilitate grasping by the user.

In still a third type of package a fine internal thread extends longitudinally of the envelope and is retained at either longitudinal end. When the envelope is torn across the end, the thread can be used as a cutting tool to tear along the length of the envelope to facilitate opening of the lateral edge of the envelope and permit removal of the bandage.

These prior art bandage packages have certain disadvantages. In the first type of package described above, the bandage is often ripped in addition to the envelope, the backing strips can be difficult to remove from fingers due to static electricity, and four pieces of refuse must be picked up and discarded. The term "refuse" as used herein refers to all left over, non-usable packaging material and protective backing strips apart from the bandage itself. In the second type of package, difficulty is often experienced in grasping the envelope end and the back-folded flap due to excitement level, arthritis, bad lighting, other reasons or combinations thereof. Once backing strips are removed from the bandage, they can again be difficult to remove from fingers due to static electricity, and four pieces of refuse must be picked up and discarded. In the third type of package described above, it is frequently found that after tearing the envelope end, the thread separates from the torn end, thereby leaving no mechanical means for tearing the envelope down its length. Tearing the envelope without the thread, or trying to grasp the fine thread is made very difficult. As with the other types of packages, the removable backing strips can be difficult to release from the user's fingers due to static electricity. Also from three to six or seven pieces of refuse must be picked up and discarded, depending on the level of difficulty experienced. The device of the present invention overcomes all of the above disadvantages eases access to the bandage, and reduces the refuse to two pieces, one of which may be retained for recycling.

All of the foregoing methods of opening conventional bandage envelopes require manipulation of thin, and frequently difficult to separate, envelope materials. These materials are discarded when the bandage has been removed, in order to permit the user to remove the flexible backing strips from the adhesive surfaces of the bandage prior to application of the bandage to a wound.

SUMMARY OF THE INVENTION

The present invention comprises a bandage device which substantially eliminates the manipulative steps required to remove the conventional prior art bandages from their envelopes. Additionally, the present invention provides a means for easier application of the bandage. In particular, the present invention provides a bandage of the well known type embodying a strip or tape, with adhesive portions adjacent each end of one surface with an intermediate gauze pad. However, in place of the traditional removable flexible backing strips applied to each adhesive half of the bandage, the present invention utilizes a primary semi-rigid backing strip which is applied to one adhesive portion and which extends beyond the end of the bandage. The semi-rigid backing strip is formed with a generally angular or pointed end sufficient to penetrate the surface of the protective paper envelope. A secondary flexible backing extends the full length of the bandage to cover the other adhesive end, any central gauze pad, and the semi-rigid strip. A portion of the flexible backing extends beyond the angular end of the rigid backing and is trapped in or attached near the end seam of the envelope proximate the tip of the semi-rigid strip. Alternatively, the flexible backing, having covered a portion of the semi-rigid backing strip, folds and returns back to be attached in or near the end seam of the envelope opposite the angular or pointed tip of the semi-rigid backing strip. A detent or boss, or grooves, or non-slip surfacing 14 protruding may be formed in the underside of the angular tip of the semi-rigid primary backing strip to facilitate grasping by the user during removal of the strip and bandage from the paper envelope.

In a further aspect of the invention, the primary backing strip may have a surface portion containing a disinfectant patch, which can be used to disinfect the wound prior to application of the bandage.

In operation, the envelope and primary backing strip are manipulated to punch or push the narrowed or pointed end of the strip through the upper face of the envelope, thereby exposing the tip end of the primary backing strip and enabling it to be grasped and removed from the envelope in a single longitudinal movement. The same movement simultaneously peels back and separates the flexible secondary backing from the bandage, thereby exposing a bandage strip with one adhesive end already exposed for application to the skin on one side of the wound, with the other end retained on the semi-rigid backing strip. Once the one adhesive end has been positioned with the gauze pad covering the wound, the semi-rigid primary backing strip is pulled away from the wound, disengaging the opposite adhesive end of the bandage which is simultaneously applied to the skin on the other side of the wound.

Where the bandage of the present invention includes the optional antiseptic patch on the primary backing strip, the antiseptic patch is exposed upon opening and removal of the bandage. The antiseptic patch can be treated to the wound prior to application of the bandage.

The bandage structure disclosed herein enables swift and convenience opening of the package, simultaneous removal of protective backings and ease of application of the adhesive bandage to a wound. Further, the present invention substantially reduces the amount of individual waste pieces.

These and other advantages of the present invention are illustrated in the accompanying drawings, wherein:

BRIEF DESCRIPTION OF THE DRAWING

FIG. 1 is a perspective view of a bandage envelope, with the bandage and backing strip inside shown in phantom;

FIG. 2 is a longitudinal cross section of the bandage and packaging prior to opening;

FIG. 2a is a longitudinal cross section of an alternate embodiment of the bandage and packaging prior to opening;

FIG. 3 is a perspective view of the same envelope after manipulation to expose the removal portion of the backing strip;

FIG. 4 is a cross-section of the bandage and packaging of the present invention after manipulation and penetration of the tab through the envelope surface;

FIG. 5 is a longitudinal cross-section of the bandage and envelope with the bandage partially removed from the envelope;

FIG. 6 is a longitudinal cross-section of the package and fully removed bandage, prior to total disengagement of the flexible backing;

FIG. 7 is a view of the bandage ready for application;

FIG. 8 is a perspective view of one form of the semi-rigid backing illustrating an optional antiseptic path.

DESCRIPTION OF PREFERRED EMBODIMENTS

In FIG. 1, it may be seen that in a bandage package, a bandage 1 is enclosed within an envelope 2 having an upper face 3 and lower face 4 which are sealed together around the peripheral edges, such as by gluing or crimping to form a seam 5. The bandage 1 is of a flexible, durable material, which may be a woven cloth such as Elastoplast TM or a plastic film. The bandage has an exterior surface and an inner or skin contacting surface. The inner surface has adhesive portions 6 and 7 located generally at respective ends of the bandage, and a gauze portion 8 intermediate the ends. The size of the bandage, and the envelope are a matter of choice, depending on the size of wound to be protected.

As may be seen in FIGS. 2 and 2a, a stiff or semi-rigid primary backing strip 9 is positioned against one adhesive undersurface, such as 6, and may extend over a portion of the gauze patch. The length of the semi-rigid strip 9 is optional, and though it is preferable to completely cover one of the adhesive portions, such as 6, its extension over the gauze portion 8 is a matter of choice. A longer strip 9, fully covering the gauze portion 8, may be used to enable easier manipulation and penetration of the envelope surface 3. The semi-rigid backing strip 9 illustrated in FIGS. 2 and 2a completely covers adhesive portion 6 and half of the gauze pad 8 for illustration purposes only.

The backing strip 9 may be made of any suitable stiff or semi-rigid material which can be sterilized, and preferably may be made of plastic, polymers, or vinyl of appropriate thickness, width and length to accommodate various size bandages.

As may be seen in FIG. 2, a thin, very flexible backing 10 covers entirely the other adhesive portion 7 and extends beyond the tip of the semi-rigid strip 9 to an end point 11 where it is retained in the seam portion 12 at the longitudinal end of the envelope 2 adjacent or proximate the backing strip 9. Alternatively, as may be seen in FIG. 2a, a thin, very flexible backing 10 covers entirely the other adhesive portion 7 and extends partially over the backing strip 9, at which point it is inverted or folded back and returns to an end point 11' where it is retained in the seam portion 12' at the longitudinal end of the envelope opposite or remote from the angular or pointed tip 13 of the semi-rigid backing 9. The seam 5 and in particular the seam 12 (or 12' as seen in FIG. 2a) may be sealed by crimping, swaging, gluing or folding together the end of flexible backing 10 and the appropriate ends of the envelope surfaces 3 and 4.

Flexible backing 10 may be of any thin and very flexible material such as plastic film or sterile paper. Again, thickness, width and length are selected to accommodate various sizes of bandages. The material will also be selected to be compatible with sterile requirement as well as to release from the adhesive of the bandage.

The backing strip 9 has a tip 13 extending beyond the longitudinal end of the bandage 1. The tip of the backing strip is generally pointed, but may have varying degrees of angle, sufficient to penetrate the envelope surface 3 while still maintaining a profile adequate to prevent injury or abrasion when manipulated by a user. The corners of the backing strip may be rounded to prevent any injury or abrasion. Optionally, the tip may include a detent or boss, 14 protruding from the undersurface of the tip 13 to facilitate grasping by the user's fingertips. Alternatively, rather than boss 14, grooves or non-slip surfacing may be utilized to improve the users grip on the tip 13.

In order to remove the bandage from the envelope, as contemplated by this invention, the envelope is grasped by the user in one hand, adjacent the mid-point in order to grip the backing strip 9 through the envelope. The end of the envelope, containing seam portion 12 and end 11 of the flexible backing strip 10, is then manipulated by the user's other hand at an angle to the plane of the backing strip to cause the tip 13 to penetrate or tear the face 3 of the envelope, as may be seen in FIGS. 3 and 4. The exposed tip 13 of the rigid backing 9 may be then gripped by the user and withdrawn lengthwise from the envelope as seen in FIG. 5.

As may be seen in FIGS. 5, 6 and 7, the bandage and rigid backing are withdrawn from the envelope causing the end 11 of the flexible backing 10 to slide away from contact with the semi-rigid backing 9, and ultimately to be peeled away from the adhesive surface 7 of the bandage 1.

Upon full removal of the bandage, the adhesive surface 7 is fully exposed for application on one side of a wound. Application may be performed single-handedly by the user, holding the tip 13 and laying the exposed adhesive end 7 against the skin surface adjacent to the wound, and then rotating the backing strip 9 to position the gauze portion over the wound. Continued tension between the backing strip 9 and the bandage, will peel the adhesive portion to form the semi-rigid backing 9. The adhesive portion 6 is guided by strip 9 and applied against the skin surface on the opposite side of the wound.

In a further embodiment of the invention, the semi-rigid strip 9 may have an antiseptic swab portion. The surface portion 15 of the strip 9 is protected by flexible backing 10. An antiseptic powder or cream may be removably adherent to the surface 15. While holding the tip 13 of the strip 9, the user may rub the swab surface portion 15 gently on the wound, thereby conveying the antiseptic to the wound.

As may be seen from FIG. 8, the backing strip 9 may have an adhesive perimeter 16 surrounding the antiseptic portion 15. The adhesive 16 with adherence to the flexible backing 10, thereby creating a sealed pocket between the backings 9 and 10 to retain the antiseptic. During removal of the bandage from the envelope 3, the flexible backing 10 will be peeled from the adhesive perimeter 16, exposing the antiseptic surface for use as a swab.

After application of the bandage as set out above, only the envelope, with its integral flexible strip 10, and the semi-rigid backing strip 9 remains as refuse for disposition.

Although the foregoing describes the invention in preferred embodiments, it will be understood that various changes in sizes and materials may be made without departure from the scope of the invention. The invention may also be applied to substrates other than bandages, such as individually packaged adhesive labels, stickers or tags.

The embodiments of the invention in which an exclusive property or privilege is claimed are as follows:

1. A package comprising a sealed envelope containing a substrate with adhesive on one surface, wherein the substrate has a primary backing strip of suitable semi-rigid material removably adhered to an end region of the substrate surface; the strip having a tip adapted to penetrate a face of the envelope; a flexible secondary backing removably adhered to the remaining portion of the substrate surface and overlying the primary backing strip; the flexible backing having an extension portion affixed to the envelope adjacent one end of the envelope.

2. The package of claim 1, wherein the extension portion extends axially beyond the tip of the primary backing strip and is affixed to the envelope adjacent the proximate end.

3. The package of claim 1, wherein the extension portion inverts towards and is affixed to the envelope adjacent the end remote from the tip.

4. The package of claim 1, wherein the substrate is a bandage.

5. The package of claim 4, wherein the surface has an adhesive portion adjacent each end of the substrate.

6. The package of claim 5, wherein the substrate includes a gauze pad between the adhesive portions.

7. The package of claims 1, wherein the envelope is sealed along a perimeter seam and the extension portion of the flexible backing is retained in the seam.

8. The package of claims 1, wherein the seam is crimped, folded or glued along a perimeter seam and the extension portion of the flexible backing is crimped in the seam.

9. A bandage package comprising a sealed envelope containing an adhesive bandage with an adhesive portion adjacent each end of the bandage wherein the bandage has a primary backing strip of suitable semi-rigid material removably adhered to one adhesive portion of the bandage; the primary backing strip having a tip adapted to penetrate a face of the envelope; a flexible secondary backing overlying the remaining portion of the adhesive bandage as well as the primary backing strip; the flexible backing having an extension portion extending axially beyond the tip of the primary backing strip and affixed to the envelope adjacent the proximate end.

10. The package of claim 9, wherein the tip extends beyond the adhesive bandage.

11. The package of claim 9, wherein the tip has a triangular point.

12. The package of claim 11, wherein the tip is truncated or rounded.

13. The package of claim 9, wherein the envelope is sealed along a perimeter seam and the extension portion of the flexible backing is retained in the seam.

14. The package of claim 13, wherein the seam is crimped, folded or glued.

15. The package of claim 9, wherein the backing strip has an antiseptic swab portion on the surface adjacent the flexible backing.

16. The package of claim 9, wherein the substrate is a label.

17. The package of claim 16, wherein the adhesive covers the entire surface of the substrate.

* * * * *